United States Patent
Kim et al.

(10) Patent No.: US 9,902,905 B2
(45) Date of Patent: Feb. 27, 2018

(54) LIQUID CRYSTAL COMPOSITION AND LIQUID CRYSTAL DISPLAY INCLUDING THE SAME

(71) Applicant: Samsung Display Co., Ltd., Yongin-si, Gyeonggi-do (KR)

(72) Inventors: Si Heun Kim, Hwaseong-si (KR); Beom-Soo Shin, Hwaseong-si (KR); Hye Lim Jang, Hwaseong-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/082,430

(22) Filed: Mar. 28, 2016

(65) Prior Publication Data
US 2016/0362604 A1    Dec. 15, 2016

(30) Foreign Application Priority Data

Jun. 12, 2015 (KR) ........................ 10-2015-0083592

(51) Int. Cl.
*G02F 1/1333* (2006.01)
*C09K 19/30* (2006.01)
(Continued)

(52) U.S. Cl.
CPC ........ *C09K 19/3003* (2013.01); *C07C 43/225* (2013.01); *C09K 19/32* (2013.01); *G02F 1/1337* (2013.01); *G02F 1/1368* (2013.01); *G02F 1/13378* (2013.01); *G02F 1/13439* (2013.01); *G02F 1/133345* (2013.01); *G02F 1/134309* (2013.01); *G02F 1/136227* (2013.01); *C07C 2601/14* (2017.05); *C07C 2602/08* (2017.05); *C09K 2019/0444* (2013.01); *C09K 2019/0466* (2013.01); *C09K 2019/123* (2013.01); *C09K 2019/301* (2013.01);
(Continued)

(58) Field of Classification Search
CPC ................ C09K 19/3003; C09K 19/32; C09K 2019/0444; C09K 2019/0466; C09K 2019/123; C09K 2019/304; C09K 2019/301; C09K 2019/3016; C09K 2019/3019; C09K 2019/3027; C09K 2019/3422; G02F 1/1333; G02F 1/133345; G02F 1/1337; G02F 1/13378; G02F 1/134309; G02F 1/13439; G02F 1/136227; G02F 1/1368; C07C 43/225; C07C 2601/14; C07C 2602/08
USPC ........................ 252/299.6; 428/1.1
See application file for complete search history.

(56) References Cited

U.S. PATENT DOCUMENTS 6,391,397 B1    5/2002    Jones et al.
6,475,595 B1    11/2002    Bremer et al.
(Continued)

FOREIGN PATENT DOCUMENTS

DE    102004030315 A1    1/2005
DE    102009011666 A1    9/2009
(Continued)

OTHER PUBLICATIONS

Goodby J W et al., "The Synthesis and Properties of Host Materials with Fluoro Substituents in the Core and in a Terminal Chain for High Dielectric Biaxiality FLC Mixtures", Ferroelectrics, 2000, vol. 243, pp. 19-26.
(Continued)

*Primary Examiner* — Geraldina Visconti
(74) *Attorney, Agent, or Firm* — Cantor Colburn LLP

(57) ABSTRACT

A liquid crystal composition includes at least one polar liquid crystal molecule represented by Chemical Formulas A or B.

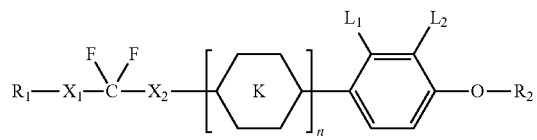

Formula A

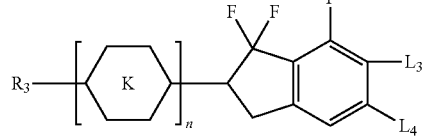

Formula B

Each K is independently 1,4-cyclohexylene or 1,4-phenylene, groups connected to carbon ring of 1,4-cyclohexylene or 1,4-phenylene are all hydrogen or at least one of the groups is fluorine, and n is 1 or 2; in Chemical Formula A, $X_1$ and $X_2$ are independently a single bond, $-CH_2-$, $-CH_2CH_2-$, $-CF_2-$, $-CH_2O-$, or $-OCH_2-$, $L_1$ and $L_2$ are independently $-H$, $-F$, $-CF_3$, or $-OCF_3$, and $R_1$ and $R_2$ are independently an alkyl or alkoxy group having 1 to 9 carbon atoms or an alkenyl group having 2 to 9 carbon atoms; in Chemical Formula B, $L_3$ and $L_4$ are independently $-H$, $-F$, $-CF_3$, or $-OCF_3$, and $R_3$ is an alkyl or alkoxy group having 1 to 9 carbon atoms or an alkenyl group having 2 to 9 carbon atoms.

20 Claims, 8 Drawing Sheets

(51) Int. Cl.
  *C09K 19/32* (2006.01)
  *C07C 43/225* (2006.01)
  *G02F 1/1337* (2006.01)
  *G02F 1/1343* (2006.01)
  *G02F 1/1362* (2006.01)
  *G02F 1/1368* (2006.01)
  *C09K 19/04* (2006.01)
  *C09K 19/12* (2006.01)
  *C09K 19/34* (2006.01)

(52) U.S. Cl.
  CPC ............... *C09K 2019/3004* (2013.01); *C09K 2019/3016* (2013.01); *C09K 2019/3019* (2013.01); *C09K 2019/3027* (2013.01); *C09K 2019/3422* (2013.01)

(56) References Cited

U.S. PATENT DOCUMENTS

| | | | |
|---|---|---|---|
| 8,168,081 B2* | 5/2012 | Klasen-Memmer ... | C09K 19/12 252/299.01 |
| 8,916,063 B2* | 12/2014 | Goto ...................... | C09K 19/12 252/299.61 |
| 9,580,652 B2* | 2/2017 | Takeshita ............ | C09K 19/3028 |
| 2011/0101270 A1* | 5/2011 | Manabe ................. | C09K 19/32 252/299.62 |
| 2014/0166931 A1 | 6/2014 | Goto et al. | |

FOREIGN PATENT DOCUMENTS

| | | |
|---|---|---|
| DE | 102009015692 A1 | 10/2009 |
| JP | 2012158626 | 8/2012 |
| KR | 1020120115534 | 10/2012 |
| KR | 1020120125255 | 11/2012 |
| KR | 1020140126289 | 10/2014 |
| WO | 03010120 A1 | 2/2003 |
| WO | 2004048500 A1 | 6/2004 |
| WO | 2005037957 A1 | 4/2005 |
| WO | 2012079710 A1 | 6/2012 |

OTHER PUBLICATIONS

Partial European Search Reported dated Nov. 7, 2016, of the corresponding European Patent Application No. 16173035.
Extended European Search Report dated Mar. 3, 2017, of the corresponding European Patent Application No. 16173035.3.

* cited by examiner

[ LC director Schematic view ]

LIQUID CRYSTAL COMPOSITION AND LIQUID CRYSTAL DISPLAY INCLUDING THE SAME

This application claims priority to Korean Patent Application No. 10-2015-0083592 filed on Jun. 12, 2015, and all the benefits accruing therefrom under 35 U.S.C. § 119, the entire content of which in its entirety is incorporated herein by reference.

BACKGROUND (a) Field

The present invention relates to a liquid crystal (LC) composition and a liquid crystal display (LCD) including the same.

(b) Description of the Related Art

A liquid crystal display (LCD), which is a widely used flat panel display, includes two sheets of display panels facing each other, a liquid crystal (LC) layer interposed therebetween, and field generating electrodes (e.g. a pixel electrode, a common electrode, etc.) disposed in at least one of the two sheets of display panels.

The LCD is configured to determine the orientation of LC molecules within an LC layer and to adjust the transmittance of light transmitted through the LC layer by applying a voltage to the field generating electrode and generating an electric field in the LC layer.

In the LCD, the composition of the LC layer plays a role in adjusting light transmittance and achieving a desired image. In particular, as the uses of the LCD are diversified, it is desirable to optimize the LC composition in order to achieve various characteristics such as low voltage driving, a high voltage holding ratio (VHR), a wide viewing angle, a wide operating temperature range, a high response speed, and high transmittance.

In order to obtain an LCD having high-speed response characteristics and high transmittance, research has been undertaken to improve the physical properties of the LC composition such as rotational viscosity, refractive index, etc.

The above information disclosed in this Background section is only to enhance the understanding of the background of the invention and therefore it may contain information that does not form the prior art that is already known in this country to a person of ordinary skill in the art.

SUMMARY

An exemplary embodiment provides a liquid crystal (LC) composition capable of improving transmittance while maintaining a driving voltage. A liquid crystal display (LCD) including the LC composition is also provided.

In an exemplary embodiment, an LC composition includes at least one polar LC molecule containing a fluorine substituent represented by Chemical Formula A or Chemical Formula B.

Chemical Formula A

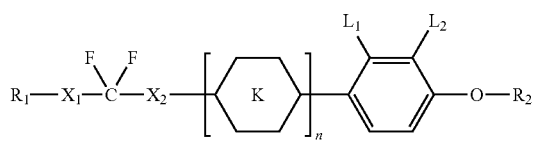

Chemical Formula B

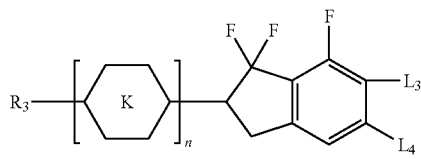

In Chemical Formulas A and B, each K is, independently of one another, 1,4-cyclohexylene or 1,4-phenylene, groups connected to a carbon ring of the 1,4-cyclohexylene or 1,4-phenylene are all hydrogen or at least one of the groups is fluorine, and n is 1 or 2; in Chemical Formula A, $X_1$ and $X_2$ are, independently of one another, a single bond, $-CH_2-$, $-CH_2CH_2-$, $-CF_2-$, $-CH_2O-$, or $-OCH_2-$, $L_1$ and $L_2$ are, independently of one another, $-H$, $-F$, $-CF_3$, or $-OCF_3$, and $R_1$ and $R_2$ are, independently of one another, an alkyl group having 1 to 9 carbon atoms, or an alkoxy group having 1 to 9 carbon atoms, or an alkenyl group having 1 to 9 carbon atoms; and in Chemical Formula B, $L_3$ and $L_4$ are, independently of one another, $-H$, $-F$, $-CF_3$, or $-OCF_3$, and $R_3$ is an alkyl or alkoxy group having 1 to 9 carbon atoms or an alkenyl group having 2 to 9 carbon atoms.

In an exemplary embodiment, the LC composition may further include at least one positive LC molecule that is represented by Chemical Formula C or Chemical Formula D.

Chemical Formula C

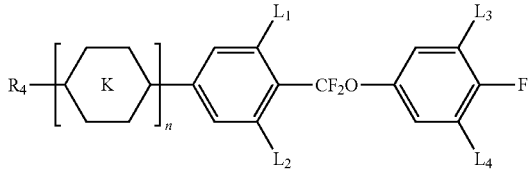

Chemical Formula D

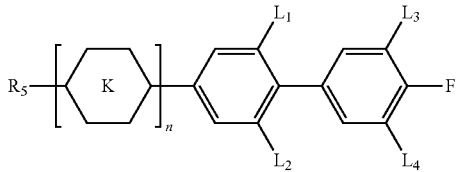

In Chemical Formula C and Chemical Formula D, each K is independently of one another, 1,4-cyclohexylene, 1,4-phenylene, tetrahydropyran, or pyran, groups connected to a carbon ring of the 1,4-cyclohexylene 1,4-phenylene, tetrahydropyran, or pyran are all hydrogen or at least one of the groups is fluorine, $L_1$ to $L_4$ are, independently of one another, $-H$, $-F$, $-CF_3$, or $-OCF_3$, n is 1 or 2, and $R_4$ and $R_5$ are, independently of one another, an alkyl or alkoxy group having 1 to 9 carbon atoms or an alkenyl group having 2 to 9 carbon atoms.

In an exemplary embodiment, the LC composition may further include at least one LC molecule that is represented by Chemical Formula E.

Chemical Formula E

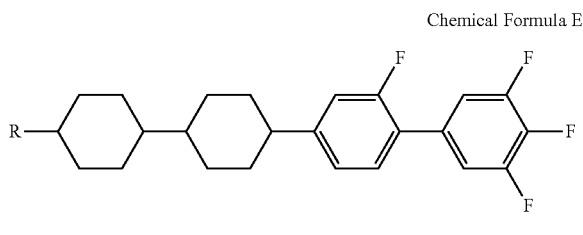

In Chemical Formula E, R is an alkyl or alkoxy group having 1 to 9 carbon atoms or an alkenyl group having 2 to 9 carbon atoms.

In an exemplary embodiment, the LC composition may further include at least one LC molecule that is represented by Chemical Formula F.

Chemical Formula F

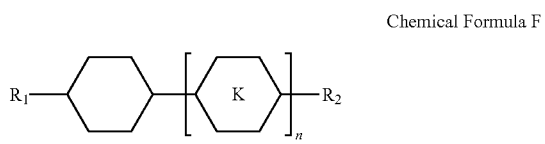

In Chemical Formula F, K is 1,4-cyclohexylene or 1,4-phenylene, $R_1$ and $R_2$ are, independently of one another, an alkyl or alkoxy group having 1 to 9 carbon atoms or an alkenyl group having 2 to 9 carbon atoms, and n is 1 or 2.

In an exemplary embodiment, the LC composition may further include at least one LC molecule that is represented by Chemical Formula G.

Chemical Formula G

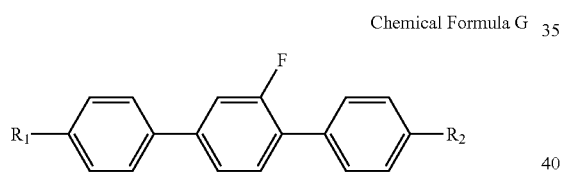

In Chemical Formula G, $R_1$ and $R_2$ are, independently of one another, an alkyl or alkoxy group having 1 to 9 carbon atoms or an alkenyl group having 2 to 9 carbon atoms.

In an exemplary embodiment, the polar LC molecule containing the fluorine substituent may be present in an amount of about 5 wt % to about 30 wt % of the total weight of the liquid crystal composition.

In exemplary embodiments, an LCD includes: a first substrate; a first electrode and a second electrode disposed on the first substrate; an insulating layer interposed between the first electrode and second electrode; a second substrate facing the first substrate; and an LC layer disposed between the first and second substrates. The LC layer includes at least one polar LC molecule containing a fluorine substituent represented by Chemical Formula A or Chemical Formula B.

Chemical Formula A

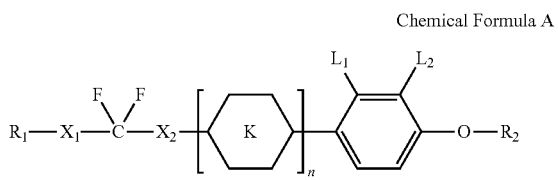

-continued

Chemical Formula B

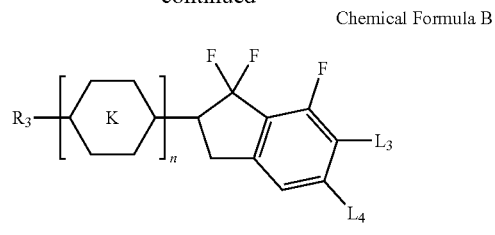

In Chemical Formulas A and B, each K is, independently of one another, 1,4-cyclohexylene or 1,4-phenylene, groups connected to a carbon ring of the 1,4-cyclohexylene or 1,4-phenylene are all hydrogen or at least one of the groups is fluorine, and n is 1 or 2; in Chemical Formula A, $X_1$ and $X_2$ are, independently of one another, a single bond, —$CH_2$—, —$CH_2CH_2$—, —$CF_2$—, —$CH_2O$—, or —$OCH_2$—, $L_1$ and $L_2$ are, independently of one another, —H, —F, —$CF_3$, or —$OCF_3$, and $R_1$ and $R_2$ are, independently of one another, an alkyl or alkoxy group having 1 to 9 carbon atoms or an alkenyl group having 2 to 9 carbon atoms; and in Chemical Formula B, $L_3$ and $L_4$ are, independently of one another, —H, —F, —$CF_3$, or —$OCF_3$, and $R_3$ is an alkyl or alkoxy group having 1 to 9 carbon atoms or an alkenyl group having 2 to 9 carbon atoms.

In an exemplary embodiment, the LC layer may further include at least one positive LC molecule that is represented by Chemical Formula C or Chemical Formula D.

Chemical Formula C

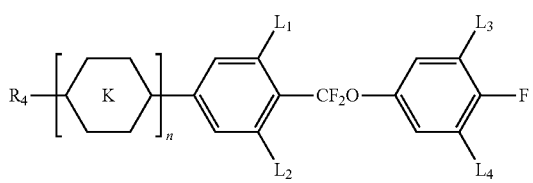

Chemical Formula D

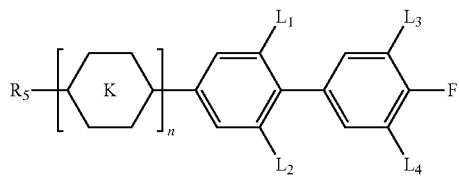

In Chemical Formula C and Chemical Formula D, each K is, independently of one another, 1,4-cyclohexylene, 1,4-phenylene, tetrahydropyran, or pyran, groups connected to a carbon ring included in 1,4-cyclohexylene, 1,4-phenylene, tetrahydropyran, or pyran are all hydrogen or at least one of the groups is fluorine, $L_1$ to $L_4$ are, independently of one another, —H, —F, —$CF_3$, or —$OCF_3$, n is 1 or 2, and $R_4$ and $R_5$ are, independently of one another, an alkyl or alkoxy group having 1 to 9 carbon atoms or an alkenyl group having 2 to 9 carbon atoms.

In an exemplary embodiment, the LC layer may further include at least one LC molecule that is represented by Chemical Formula E.

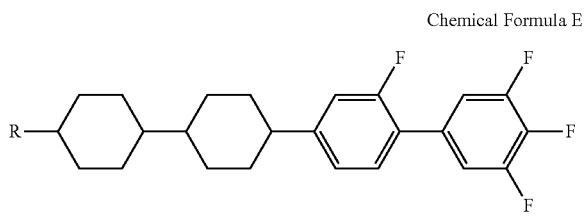

Chemical Formula E

In Chemical Formula E, R is an alkyl or alkoxy group having 1 to 9 carbon atoms or an alkenyl group having 2 to 9 carbon atoms.

In an exemplary embodiment, the LC layer may further include at least one LC molecule that is represented by Chemical Formula F.

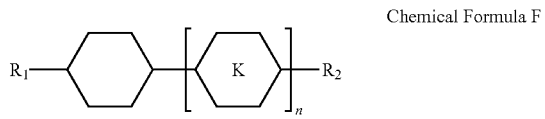

Chemical Formula F

In Chemical Formula F, K is 1,4-cyclohexylene or 1,4-phenylene, $R_1$ and $R_2$ are, independently of one another, an alkyl or alkoxy group having 1 to 9 carbon atoms or an alkenyl group having 2 to 9 carbon atoms, and n is 1 or 2.

In an exemplary embodiment, the LC layer may further include at least one LC molecule that is represented by Chemical Formula G.

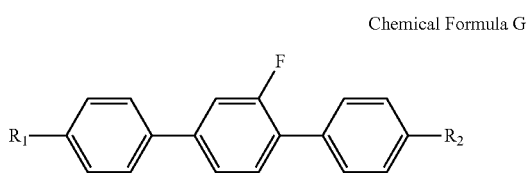

Chemical Formula G

In Chemical Formula G, $R_1$ and $R_2$ are, independently of one another, an alkyl or alkoxy group having 1 to 9 carbon atoms or an alkenyl group having 2 to 9 carbon atoms.

In an exemplary embodiment, the polar LC molecule containing a fluorine substituent may be present in an amount of about 5 wt % to about 30 wt % of the total weight of the liquid crystal layer.

In an exemplary embodiment, the insulating layer may be disposed on the first electrode, and the second electrode may be disposed on the insulating layer.

In an exemplary embodiment, the first electrode may be plate-shaped, and the second electrode may include a plurality of branch electrodes.

In an exemplary embodiment, the plurality of branch electrodes may overlap the plate-shaped first electrode.

In an exemplary embodiment, the second electrode may be electrically connected to a thin film transistor by a contact hole defined in the insulating layer.

In an exemplary embodiment, the LC molecules included in the LC layer may be tilted in a direction parallel to the branch electrodes when no electric field is applied to the LC layer.

In an exemplary embodiment, the LCD may further include an alignment layer that is disposed on the second electrode, and the alignment layer may be rubbed or photo-aligned to be parallel to the branch electrodes.

In an exemplary embodiment, when an electric field is applied to the LC layer, the LC molecules are tilted in a direction parallel to the electric field.

The first electrode may be plate-shaped in a portion that corresponds to a unit pixel.

According to the various exemplary embodiments, the exemplary LC composition including the polar LC molecule described herein may be used in a positive type of in-plane switching (IPS) mode LCD, thereby improving the driving voltage of the LCD while maintaining transmittance.

BRIEF DESCRIPTION OF THE DRAWINGS

The above and other advantages and features of this disclosure will become more apparent by describing in further detail exemplary embodiments thereof with reference to the accompanying drawings, in which.

DETAILED DESCRIPTION

Figure 1:
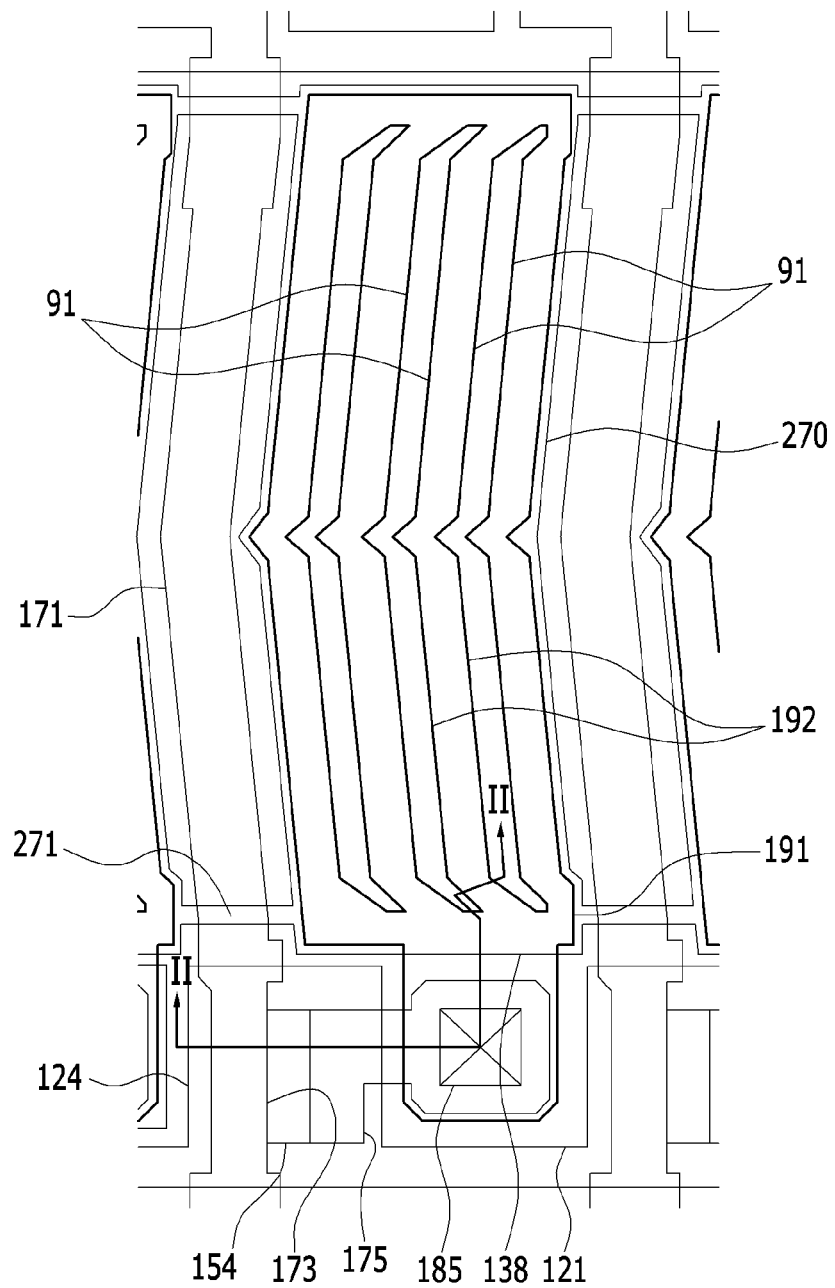
FIG. 1 is a top plan view of an exemplary liquid crystal display (LCD).

The present invention will now be described more fully hereinafter with reference to the accompanying drawings, in which exemplary embodiments are shown. As those skilled in the art would realize, the described embodiments may be modified in various different ways, all without departing from the spirit or scope of the present invention. On the contrary, exemplary embodiments introduced herein are provided to make disclosed contents thorough and complete and to sufficiently transfer the spirit of the present invention to those skilled in the art.

In the drawings, the thickness of layers and regions may be exaggerated for clarity. In addition, when a layer is described to be formed on another layer or substrate, this means that the layer may be formed directly on the other layer or substrate, or a third layer may be interposed between the layer and the other layer or the substrate. Like reference numerals designate like elements throughout the specification.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

In an exemplary embodiment, a liquid crystal (LC) composition includes at least one polar LC molecule containing a fluorine substituent and is represented by Chemical Formula A or Chemical Formula B.

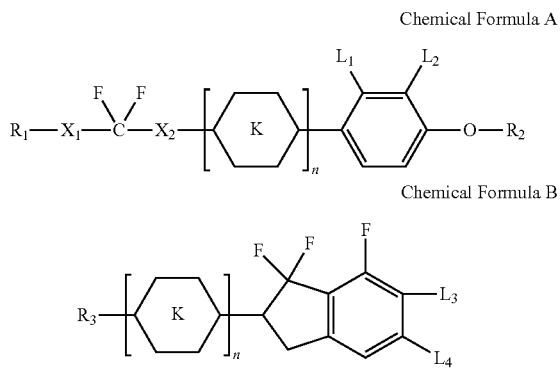

Chemical Formula A

Chemical Formula B

In Chemical Formulas A and B, each K, independently of one another, is 1,4-cyclohexylene or 1,4-phenylene. The groups connected to the carbon ring included in the 1,4-cyclohexylene or 1,4-phenylene are all hydrogen or at least one of the groups is fluorine, and n is 1 or 2. In Chemical Formula A, $X_1$ and $X_2$ are, independently of one another, a single bond, —$CH_2$-, —$CH_2CH_2$-, —$CF_2$-, —$CH_2O$—, or —$OCH_2$-; $L_1$ and $L_2$ are, independently of one another, —H, —F, —$CF_3$, or —$OCF_3$; and $R_1$ and $R_2$ are, independently of one another, an alkyl or alkoxy group having 1 to 9 carbon atoms or an alkenyl group having 2 to 9 carbon atoms; and in Chemical Formula B, $L_3$ and $L_4$ are, independently of one another, —H, —F, —$CF_3$, or —$OCF_3$, and $R_3$ is an alkyl or alkoxy group having 1 to 9 carbon atoms or an alkenyl group having 2 to 9 carbon atoms.

In an exemplary embodiment, the polar LC molecule including a fluorine substituent may have additional polarity in a direction of a minor axis as compared with the polar LC molecule of a comparative example that is represented by Chemical Formula R.

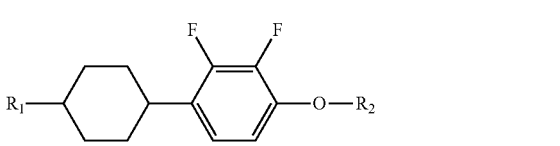

Chemical Formula R

In Chemical Formula R, $R_1$ and $R_2$ are, independently of one another, an alkyl or alkoxy group having 1 to 9 carbon atoms or an alkenyl group having 2 to 9 carbon atoms.

Specifically, in Chemical Formulas A and B, components of the polar LC molecule are connected to one another in a direction along a major axis, i.e., a horizontal direction, and the two fluorine atoms are distributed on one side of the axis (i.e., one-sided distributed) in a direction along a minor axis, thereby resulting in increased polarity in the direction of the minor axis. In particular in Chemical Formulas A and B, the two fluorine atoms are present on an aliphatic carbon atom, rather than a more freely rotating phenyl carbon atom.

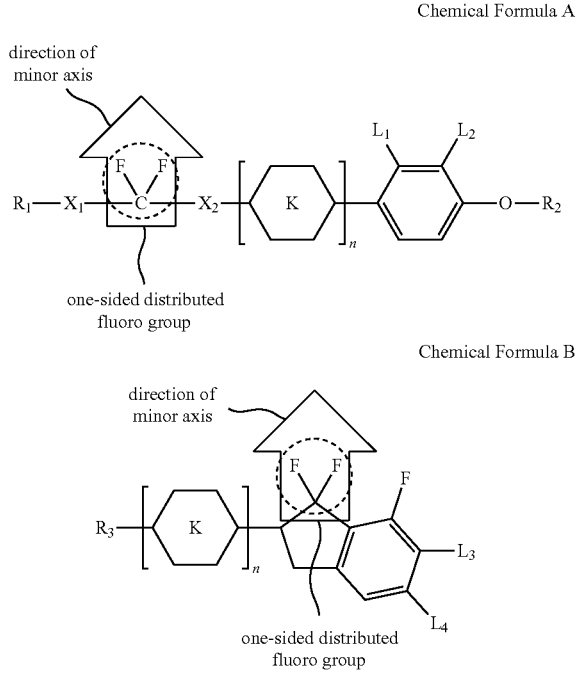

Chemical Formula A

Chemical Formula B

In an exemplary embodiment, the polar LC molecule containing the one-sided distributed fluorine substituent may be present in an amount of about 5 wt % to about 30 wt % of the total weight of the LC composition. When this amount of the one-sided distributed polar LC molecule containing the fluorine substituent is added to the LC composition, desired physical properties may be obtained. However, if the amount of the polar LC molecule exceeds 30 wt %, the liquid crystal composition may fail to produce an LC phase.

In an exemplary embodiment, a vertical dielectric constant ($\epsilon\perp$) of the one-sided distributed polar LC molecule containing the fluorine substituent may be approximately 9 or more. As used herein, the vertical dielectric constant refers to the dielectric constant in the direction of the minor axis of the molecule.

The compounds represented by Chemical Formula A may be formed according to the Synthesis Example shown below. However, the synthesis method is not limited to this exemplary embodiment, and various alternative synthesis methods may also be used to form the compounds of Chemical Formula A.

Synthesis Example

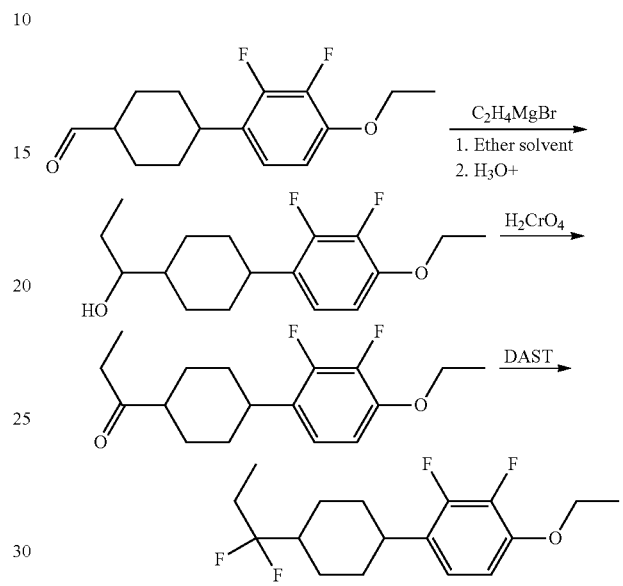

The fluorination reagent "DAST" indicated in the Synthesis Example is N,N-diethylaminosulfur trifluoride. In the current exemplary embodiment, DAST may be used as a reagent for performing fluorine substitution by deoxygenating the carbonyl. However, the reagent is not limited thereto and other reagents that are more stable in a solid form may be used instead of DAST to perform fluorine substitution of the carbonyl. Examples of other fluorination reagents include $SeF_4$, DAST DeoxoFluor®, N,N-dimethyl-1,1,2,2-tetrafluoroethylamine (TFEDMA), XtalFluor-E®, XtalFluor-M®, and FluoLead®.

Table 1 shows the corresponding phase transition temperature (Tni), refractive anisotropy (Dn), horizontal dielectric constant ($\epsilon\|$), vertical dielectric constant ($\epsilon\perp$), and rotational viscosity (Y1) of Chemical Formula R-1 (an example of Chemical Formula R), Chemical Formula A-1 (an example of Chemical Formula A), and Chemical Formula B-2 (an example of Chemical Formula B). In Table 1, $\Delta\epsilon$ refers to the difference between the horizontal dielectric constant and the vertical dielectric constant.

TABLE 1

| | Structural Formula | Tni (° C.) | Dn | $\epsilon\|$ | $\epsilon\perp$ | $\Delta\epsilon$ | Y1 (mPa•s)* |
|---|---|---|---|---|---|---|---|
| Chemical Formula R-1 | $C_3H_7$—⬡—⬢(F,F)—O—$C_2H_5$ | -3 | 0.07 | 3 | 9.7 | -6.7 | 122 |

TABLE 1-continued

| | Structural Formula | Tni (° C.) | Dn | $\epsilon_\parallel$ | $\epsilon_\perp$ | Δε | Y1 (mPa·s)* |
|---|---|---|---|---|---|---|---|
| Chemical Formula A-1 | (structure) | -15 | 0.06 | 3 | 12 | -9.0 | 236 |
| Chemical Formula B-1 | (structure) | 112 | 0.09 | 2.9 | 13.4 | -10.5 | 284 |

*millipascal-second

Referring to Table 1, Chemical Formula R-1 represents a series of LC molecules having the highest polarity. The exemplary LC molecules represented by Chemical Formula A-1 and Chemical Formula B-1 have almost the same horizontal dielectric constant ($\epsilon_\parallel$) as those represented by Chemical Formula R-1, but has relatively high negative dielectric anisotropy due to a greater vertical dielectric constant ($\epsilon_\perp$).

In an exemplary embodiment, the LC composition may further include at least one positive LC molecule that is represented by Chemical Formula C or Chemical Formula D.

Chemical Formula C

Chemical Formula D

In Chemical Formula C and Chemical Formula D, each K, independently, is 1,4-cyclohexylene, 1,4-phenylene, tetrahydropyran, or pyran, and groups connected to a carbon ring of the 1,4-cyclohexylene, 1,4-phenylene, tetrahydropyran, or pyran are all hydrogen or at least one of the groups is fluorine; $L_1$ to $L_4$ are, independently of one another, —H, —F, —CF$_3$, or —OCF$_3$; n is 1 or 2; and $R_4$ and $R_5$ are, independently of one another, an alkyl or alkoxy group having carbon 1 to 9 atoms or an alkenyl group having 2 to 9 carbon atoms.

The LC molecule represented by Chemical Formula C and the LC molecule represented by Chemical Formula D serve to maintain the dielectric anisotropy of the total LC composition. Specifically, since the LC molecule represented by Chemical Formula C and the LC molecule represented by Chemical Formula D have a positive polarity and a high dielectric constant, they may be offset by the exemplary negative LC molecule including the one-sided distributed fluorine substituent so as to not negatively impact the dielectric anisotropy.

In an exemplary embodiment, at least one of the positive LC molecules represented by Chemical Formula C or Chemical Formula D may be present in an amount of about 10 wt % to 30 wt % of the total weight of the LC composition.

In an exemplary embodiment, the horizontal dielectric constant ($\epsilon_\parallel$) of at least one of the positive LC molecules represented by Chemical Formula C or Chemical Formula D may be approximately 20 or more.

The positive LC molecule represented by Chemical Formula C may have a structure represented by Chemical Formula C-1, Chemical Formula C-2, and Chemical Formula C-3.

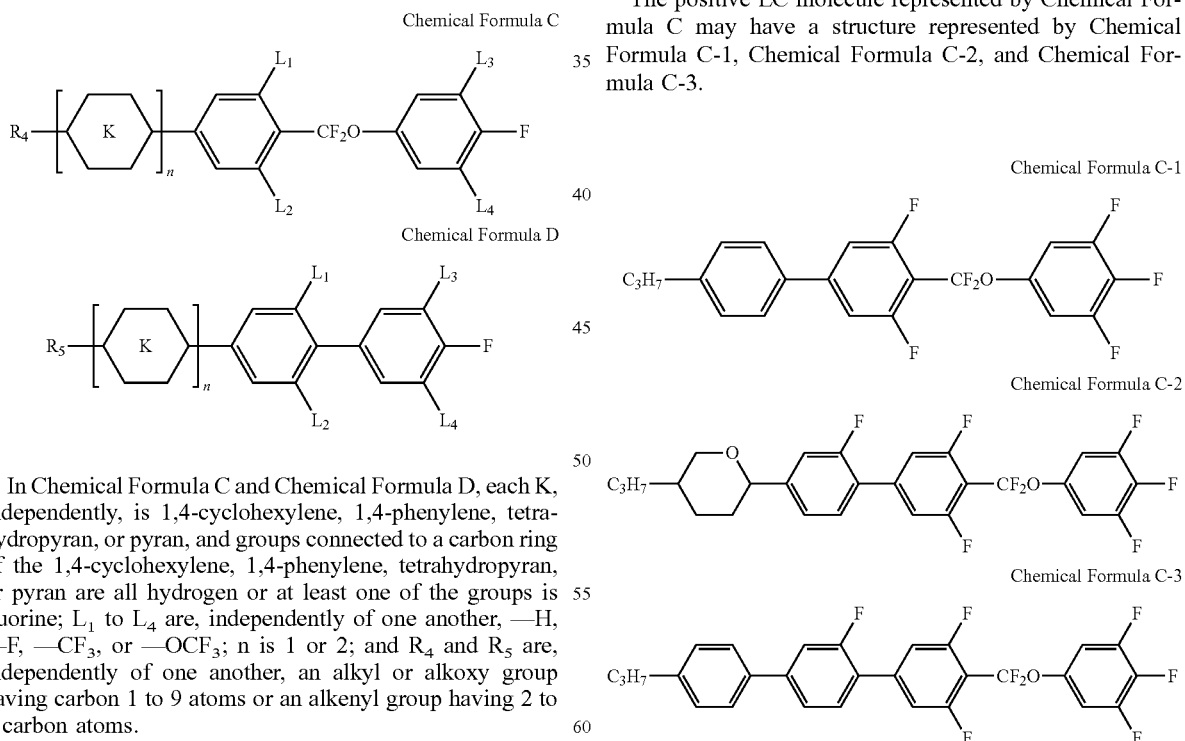

Chemical Formula C-1

Chemical Formula C-2

Chemical Formula C-3

The positive LC molecule represented by Chemical Formula D may have a structure represented by Chemical Formula D-1.

Chemical Formula D-1

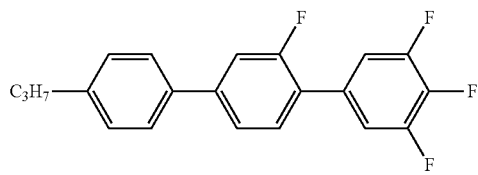

Chemical Formula E-1

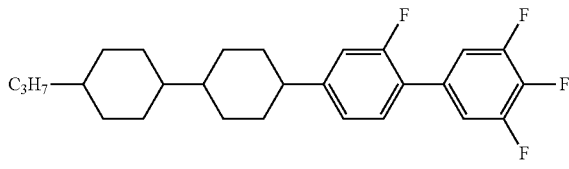

Table 2 shows the phase transition temperature (Tni), refractive anisotropy (Dn), horizontal dielectric constant (∈∥), vertical dielectric constant (∈⊥), and rotational viscosity (Y1) for each of the LC molecules having a structure represented by Chemical Formula C-1, Chemical Formula C-2, Chemical Formula C-3, and Chemical Formula D-1.

TABLE 2

|  | Tni (° C.) | Dn | ∈∥ | ∈⊥ | Δ∈ | Y1 (mPa · s) |
|---|---|---|---|---|---|---|
| Chemical Formula C-1 | 0 | 0.13 | 25.6 | 3.0 | 22.6 | 36 |
| Chemical Formula D-1 | 48 | 0.21 | 23.4 | 3.0 | 20.4 | 101 |
| Chemical Formula C-2 | 100 | 0.15 | 33.2 | 3.2 | 30.0 | 200 |
| Chemical Formula C-3 | 99 | 0.20 | 34.2 | 3.2 | 31.0 | 231 |

Referring to Table 2, the positive LC molecules represented by Chemical Formula C-1, Chemical Formula C-2, Chemical Formula C-3, and Chemical Formula D-1 have a positive dielectric anisotropy of 20 or more.

In an exemplary embodiment, the LC composition may further include at least one LC molecule that is represented by Chemical Formula E.

Chemical Formula E

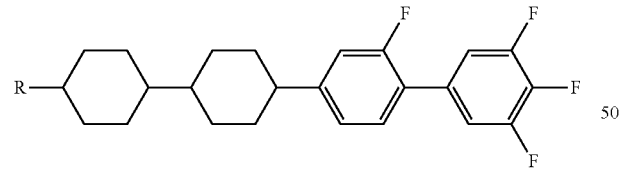

In Chemical Formula E, R is an alkyl or alkoxy group having 1 to 9 carbon atoms or an alkenyl group having 2 to 9 carbon atoms.

The LC molecule represented by Chemical Formula E serves to adjust the phase transition temperature (Tni) of the total LC composition.

In an exemplary embodiment, the LC molecule represented by Chemical Formula E may be present in an amount of about 10 wt % or less of the total weight of the LC composition.

The LC molecule represented by Chemical Formula E may have a structure represented by Chemical Formula E-1.

Table 3 shows the phase transition temperature (Tni), refractive anisotropy (Dn), horizontal dielectric constant (∈∥), vertical dielectric constant (∈⊥), and rotational viscosity (Y1) of the LC molecule having a structure represented by Chemical Formula E-1.

TABLE 3

| Tni (° C.) | Dn | ∈∥ | ∈⊥ | Δ∈ | Y1 (mPa · s) |
|---|---|---|---|---|---|
| 195 | 0.15 | 17.9 | 3.0 | 14.9 | 286 |

Referring to Table 3, the phase transition temperature (Tni) of the LC molecule represented by Chemical Formula E-1 is 195, which is relatively high.

In an exemplary embodiment, the LC composition may further include at least one LC molecule that is represented by Chemical Formula F.

Chemical Formula F

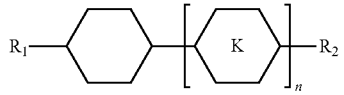

In Chemical Formula F, K is 1,4-cyclohexylene, or 1,4-phenylene, $R_1$ and $R_2$ are, independently of one another, an alkyl or alkoxy group having 1 to 9 carbon atoms or an alkenyl group having 2 to 9 carbon atoms, and n is 1 or 2.

The LC molecule represented by Chemical Formula F may have a structure represented by Chemical Formula F-1 and Chemical Formula F-2.

Chemical Formula F-1

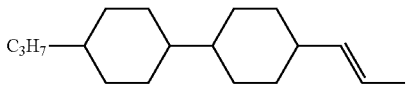

Chemical Formula F-2

In an exemplary embodiment, the LC composition t may further include at least one LC molecule that is represented by Chemical Formula G.

Chemical Formula G

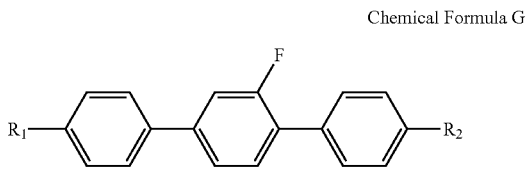

In Chemical Formula G, $R_1$ and $R_2$ are, independently of one another, an alkyl or alkoxy group having 1 to 9 carbon atoms or an alkenyl group having 2 to 9 carbon atoms.

The LC molecule represented by Chemical Formula G serves to adjust the phase transition temperature and refractive anisotropy (Dn) of the total LC composition.

In an exemplary embodiment, the LC molecule represented by Chemical Formula G may be present in an amount of about 5 to about 20 wt % or less based on the total weight of the LC composition.

The LC molecule represented by Chemical Formula G may have a structure represented by Chemical Formula G-1.

Chemical Formula G-1

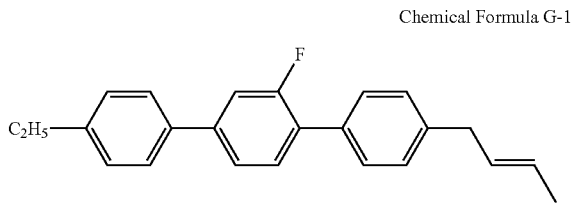

Table 4 shows the phase transition temperature (Tni), refractive anisotropy (Dn), horizontal dielectric constant (∈∥), vertical dielectric constant (∈⊥), and rotational viscosity (Y1) of each of the LC molecules having a structure represented by Chemical Formula F-1, Chemical Formula F-2, and Chemical Formula G-1.

TABLE 4

|  | Tni (° C.) | Dn | ∈∥ | ∈⊥ | Δ∈ | Y1 (mPa · s) |
| --- | --- | --- | --- | --- | --- | --- |
| Chemical Formula F-1 | 42 | 0.04 | 2.5 | 3.0 | −0.5 | 16 |
| Chemical Formula F-2 | 160 | 0.19 | 2.5 | 3.0 | −0.5 | 200 |
| Chemical Formula G-1 | 140 | 0.27 | 2.5 | 3.0 | −0.5 | 78 |

Referring to Table 4, the LC molecule represented by Chemical Formula G-1 has a phase transition temperature (Tni) of 140 and a refractive anisotropy (Dn) of 0.27, which are relatively high.

A liquid crystal display (LCD) formed using the LC composition described above will now be described with reference to the figures.

Figure 2:
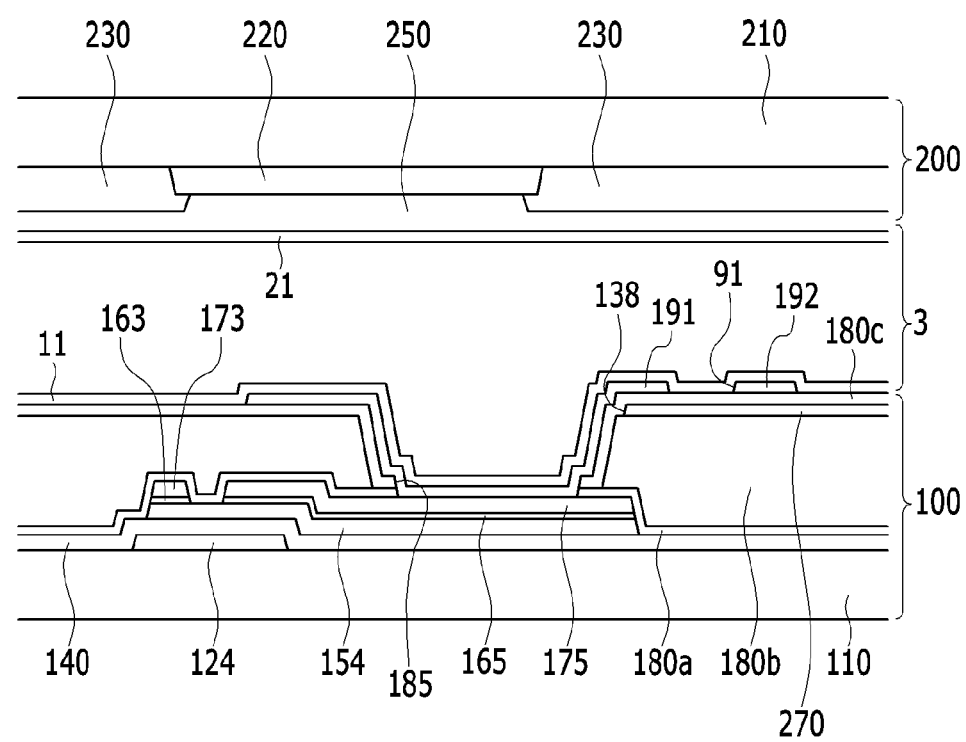
FIG. 2 is a cross-sectional view of FIG. 1 taken along the line II-II.

FIG. 1 is a top plan view of an exemplary embodiment of an LCD. FIG. 2 is a cross-sectional view of FIG. 1 taken along the line II-II.

Referring to FIGS. 1 and 2, the exemplary LCD includes lower and upper panels 100 and 200 facing each other, and an LC layer 3 interposed therebetween.

The lower panel 100 will be described first.

A gate conductor including a gate line 121 is formed on a first substrate 110 that is formed of transparent glass or plastic.

The gate line 121 may include a gate electrode 124 and a wide end portion (not shown) for connection with another layer or an external driving circuit. The gate line 121 may be made of an aluminum-based metal such as aluminum (Al) or an aluminum alloy, a silver-based metal such as silver (Ag) or a silver alloy, a copper-based metal such as copper (Cu) or a copper alloy, a molybdenum-based metal such as molybdenum (Mo) or a molybdenum alloy, chromium (Cr), tantalum (Ta), titanium (Ti), etc. The gate line 121 may have a single layer structure, or may have a multilayer structure in which at least two conductive layers having different physical properties are included.

A gate insulating layer 140 that is formed of a silicon nitride (SiNx) or a silicon oxide (SiOx) is formed on the gate line 121. The gate insulating layer 140 may have a multi-layer structure in which at least two insulating layers having different physical properties are included.

A semiconductor layer 154 that is formed of amorphous silicon or polysilicon is disposed on the gate insulating layer 140. The semiconductor layer 154 may also be formed of an oxide semiconductor.

Ohmic contacts 163 and 165 are formed on the semiconductor layer 154. The ohmic contacts 163 and 165 may be made of a material such as n+ hydrogenated amorphous silicon in which an n-type impurity such as phosphorus is doped at a high concentration, or a silicide. The ohmic contacts 163 and 165 may be paired to be disposed on the semiconductor layer 154. The ohmic contacts 163 and 165 may be omitted if the semiconductor layer 154 is an oxide semiconductor.

Data conductors including a data line 171 which includes a source electrode 173 and a drain electrode 175 are formed on the ohmic contacts 163 and 165 and the gate insulating layer 140.

The data line 171 includes a wide end portion (not shown) for connection with another layer or an external driving circuit. The data line 171 transmits a data signal, and substantially extends in a vertical direction to cross the gate line 121.

In this case, the data line 171 may include curved portions that are curved to obtain maximum transmittance of the LCD, and the curved portions may meet each other in a middle region of the pixel area to form a V-shape.

The source electrode 173 is a part of the data line 171, and is disposed on the same line as the data line 171. The drain electrode 175 is formed such that it extends in a direction to be parallel to the source electrode 173. Accordingly, the drain electrode 175 is in parallel with a portion of the data line 171.

The gate electrode 124, the source electrode 173, and the drain electrode 175 form one thin film transistor along with the semiconductor layer 154. A channel of the thin film transistor is formed in a portion of the semiconductor layer 154 between the source electrode 173 and the drain electrode 175.

Since the exemplary embodiment of an LCD includes the source electrode 173 disposed on the same line as the data line 171 and the drain electrode 175 extending in parallel with the data line 171, a width of the thin film transistor may be increased even without increasing an area occupied by the data conductor, thereby increasing the aperture ratio of the LCD.

The data line 171 and the drain electrode 175 may be formed of a refractory metal such as molybdenum, chromium, tantalum, titanium, etc., or an alloy thereof, and may have a multilayer structure (not shown) in which a refractory metal layer and a low resistance conductive layer are included. In exemplary embodiments, the multilayer structure may be a double layer of a chromium or molybdenum (alloy) lower layer and an aluminum (alloy) upper layer, or a triple layer of a molybdenum (alloy) lower layer, an aluminum (alloy) middle layer, and a molybdenum (alloy) upper layer.

A first passivation layer 180a is disposed on the data conductors 171, 173, and 175, the gate insulating layer 140, and an exposed portion of the semiconductor 154. The first passivation layer 180a may be formed of an organic material or an inorganic insulating material.

A second passivation layer 180b is formed on the first passivation layer 180a. The second passivation layer 180b may be formed of an organic insulating material.

The second passivation layer 180b may be a color filter and may exhibit one of the primary colors. The primary colors may be, for example, three primary colors, such as red, green, and blue, or yellow, cyan, and magenta, and the like. A color filter 230 for exhibiting mixed colors of the primary colors or white as well as the primary colors, may be further included. If the second passivation layer 180b is the color filter, the color filter 230 may be omitted in the upper panel 200 (described below). Alternatively, the second passivation layer 180b may be formed of an organic insulating material, and the color filter 230 may be formed between the first and second passivation layers 180a and 180b.

A common electrode 270 is disposed on the second passivation layer 180b. The common electrode 270 may be formed as a whole plate on the entire substrate 110 while having a planar shape, and includes an opening 138 that is disposed in a region corresponding to a periphery of the drain electrode 175. The opening 138 may extend in a direction parallel to the gate line 121, and may also be formed as a separated portion that overlaps the data line 171. That is, in the current exemplary embodiment, the common electrode 270 may have a plate shape that is not divided but is connected in a region corresponding to a unit pixel. In this case, portions of the common electrodes 270 of the pixels neighboring each other in a direction toward the gate line 121 may be connected to each other via a connecting portion 271.

The common electrodes 270 disposed in adjacent pixels are connected to each other, and may be provided with a constant common voltage that is supplied from the outside.

An insulating layer 180c is disposed on the common electrode 270. The insulating layer 180c may be formed of an organic material or an inorganic insulating material.

A pixel electrode 191 is disposed on the insulating layer 180c. A pixel electrode 191 includes a curved edge that is substantially parallel to the curved portion of the data line 171. The pixel electrode 191 has a plurality of cutouts 91, and includes a plurality of branch electrodes 192 that are disposed between the neighboring cutouts 91. The plurality of branch electrodes 192 overlaps the common electrode 270 when viewed from a planar view.

The pixel electrode 191 is a first field generating electrode or a first electrode, while the common electrode 270 is a second field generating electrode or a second electrode. The pixel electrode 191 and the common electrode 270 may generate a fringe field and the like.

A contact hole 185 exposing the drain electrode 175 is formed in the first passivation layer 180a, the second passivation layer 180b, and the insulating layer 180c. The pixel electrode 191 is physically and electrically connected to the drain electrode 175 via the contact hole 185, and receives a voltage from the drain electrode 175.

A first alignment layer 11 is formed on the pixel electrode 191 and the insulating layer 180c. The first alignment layer 11 may be a horizontal alignment layer, and is rubbed in a predetermined direction. However, the first alignment layer 11 is not limited to the rubbed alignment layer, and may also be formed as a photoalignment layer.

The upper panel 200 will now be described.

A light blocking member 220 is formed on a surface of a second substrate 210 that faces the first substrate 110. The second substrate 210 may be formed of transparent glass or plastic. The light blocking member 220 is referred to as a black matrix, and serves to prevent leakage of light.

A plurality of color filters 230 are also formed on a surface of the second substrate 210, the surface being the one facing the first substrate 110. When the second passivation layer 180b of the lower panel 100 is a color filter, or when a color filter is formed in the lower panel 100, the color filter 230 of the upper panel 200 may be omitted. In addition, the light blocking member 220 of the upper panel 200 may also be formed on the lower panel 100.

An overcoat 250 is formed on the color filter 230 and the light blocking member 220, and the overcoat 250 faces the first substrate 110. The overcoat 250 may be made of an (organic) insulating material, and prevents the color filter 230 from being exposed and provides a smooth surface. The overcoat 250 is optional and may be omitted.

A second alignment layer 21 is formed between the overcoat 250 and the liquid crystal layer 3. The second alignment layer 21 may be formed of the same material as the first alignment layer 11.

The LC layer 3 is interposed between the lower panel 100 and the upper panel 200. In the current exemplary embodiment, the LC layer 3 includes the polar LC molecules containing the one-sided distributed fluorine substituent, and specifically, the above description of the LC composition may be applied to the LC layer.

Figure 3:
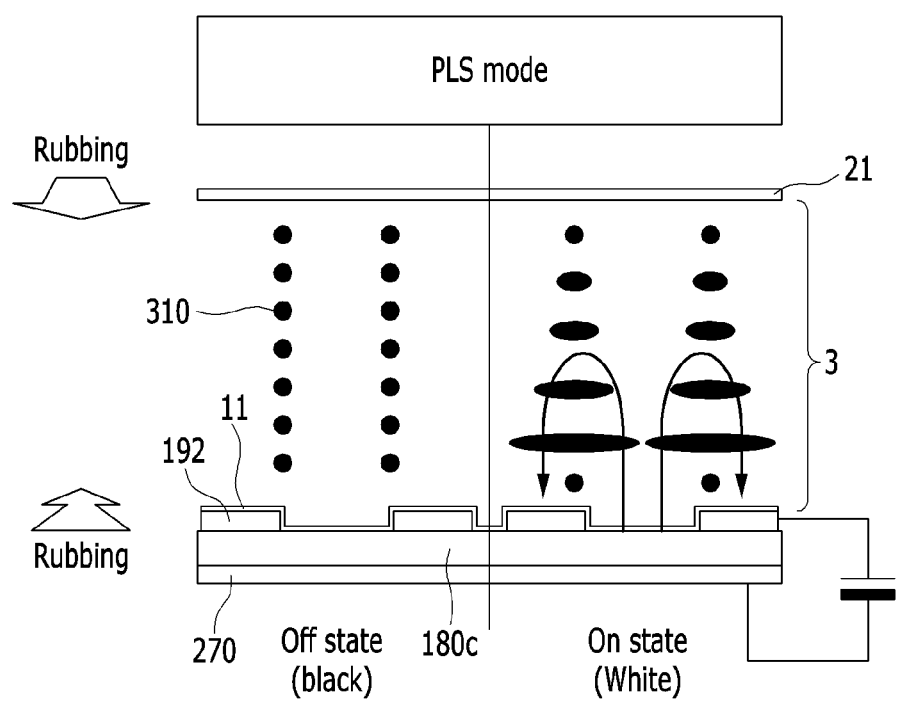
FIG. 3 is a schematic cross-sectional view showing the orientation of liquid crystal (LC) molecules in the presence or absence of an electric field in the exemplary plane-to-line switching (PLS) mode LCD.

FIG. 3 is a schematic cross-sectional view illustrating the orientation of exemplary liquid crystal (LC) molecules in the LC layer depending on the presence or absence of an electric field in the LCD.

Referring to FIG. 3, the first and second alignment layers 11 and 21 according to the current exemplary embodiment may be rubbed to be parallel to the plurality of branch electrodes 192. However, when the first and second alignment layers 11 and 21 are formed of a photo-alignment material, surfaces of the first and second alignment layers 11 and 21 may be photo-aligned to be parallel to the plurality of branch electrodes 192.

LC molecules 310 of the LC layer 3 may be arranged such that their long axes are parallel to the display panels 100 and 200. Particularly, according to the current exemplary embodiment, the long axes of the LC molecules 310 may be arranged to be parallel to the plurality of branch electrodes 192 in an "off" state in which no electric field is applied. In other words, the LC molecules 310 are tilted in the same direction in which the branch electrode 192 extends.

In the current exemplary embodiment, the long axes of the LC molecules 310 may be aligned to be parallel to the electric field in an "on" state in which an electric field is applied. The exemplary LCD is a positive type, in-plane switching (IPS) mode LCD, and therefore, the LC layer 3 may be formed of an LC material, of which the total LC composition has a positive polarity. The LCD illustrated in FIG. 3 is specifically a plane-to-line switching (PLS) mode LCD in which a planar field generating electrode and a linear field generating electrode generate the electric field of the LC layer 3 with the insulating layer interposed therebetween. Such a positive type of IPS mode LCD has a problem in that transmittance generally decreases in an open portion between the branch electrode 192 and the neighboring branch electrode 192. However, without being limited by theory, since the exemplary LC composition includes the positive LC molecules including the one-sided distributed fluorine substituent, an average dielectric constant of the total LC composition may increase, thereby increasing the transmittance of the LCD.

Figure 4:
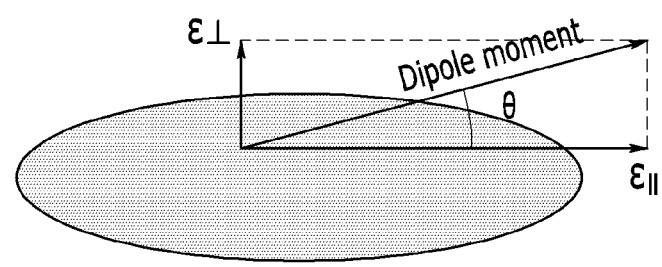
FIG. 4 is a drawing schematically illustrating LC directors.
Figure 5A:
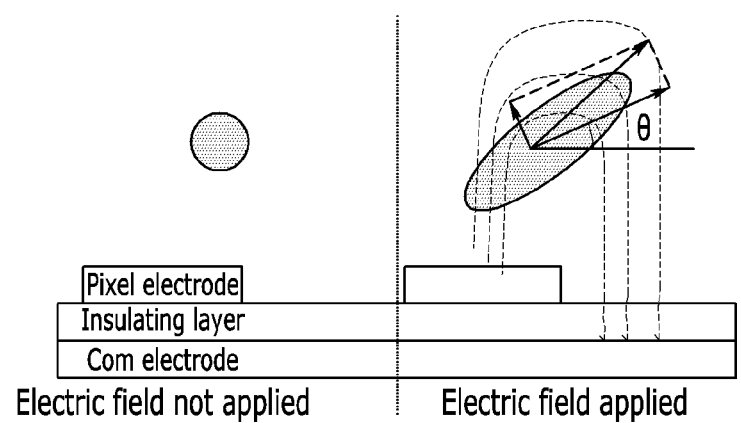
FIGS. 5A and 5B are drawings illustrating the relationship between dielectric constant and transmittance of a vertical component of the LC molecule.
Figure 5B:
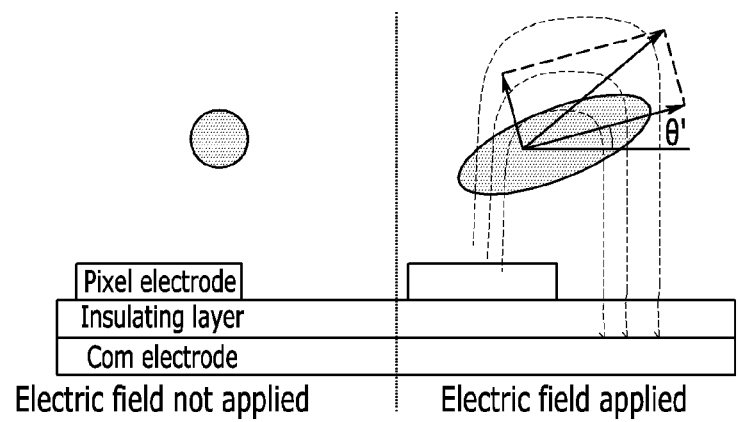
Figure 6:
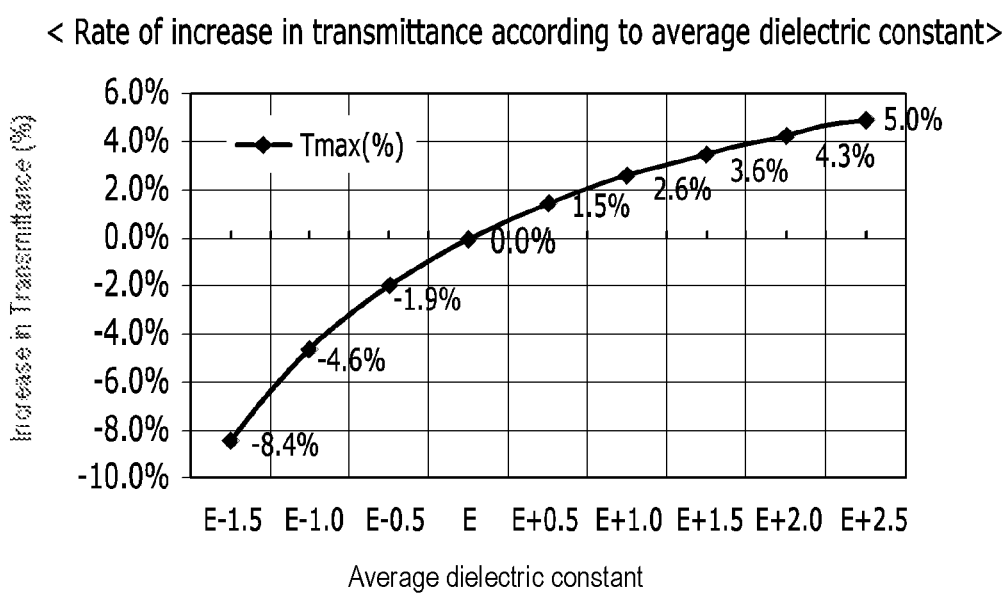
FIG. 6 is a graph illustrating the average dielectric constant versus rate of increase in transmittance (%) for an LC composition.
Figure 7:
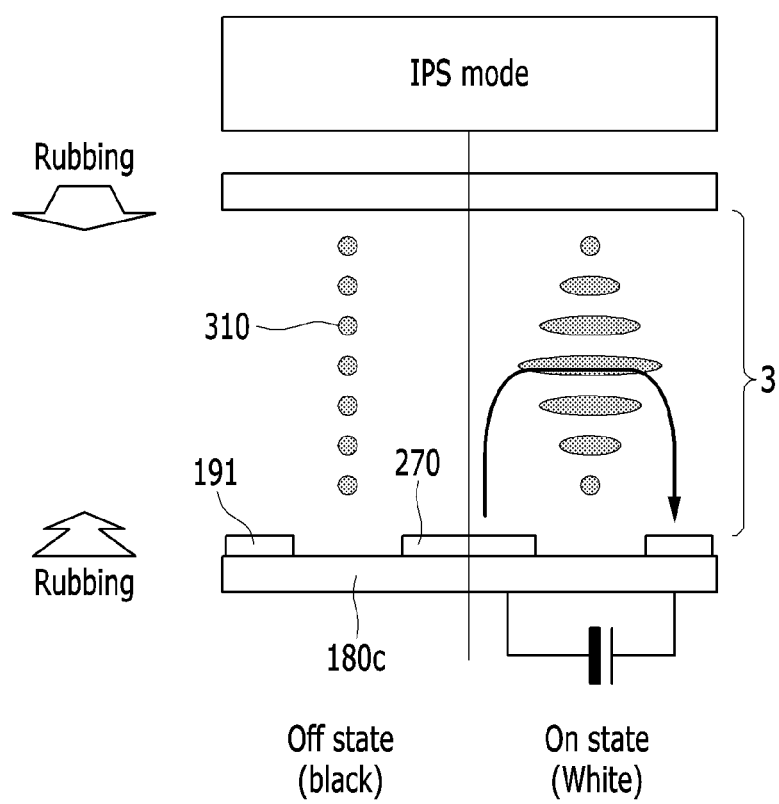
FIG. 7 is a schematic cross-sectional view of an exemplary in-plane switching (IPS) mode LCD that is a modification of the exemplary embodiment of FIG. 3.

Referring to FIGS. 4 and 5, the relationship between the vertical dielectric constant ($\epsilon\perp$) and the transmittance of the LC molecule is described. Referring to FIGS. 6 to 8, in the positive type of IPS mode LCD, transmittance according to an average dielectric constant will be described.

FIG. 4 is a drawing that schematically illustrates LC directors. FIGS. 5A and 5B are drawings that illustrate a relationship between a dielectric constant and transmittance of a vertical component of the LC molecule.

Referring to FIG. 4, as the vertical dielectric constant ($\epsilon\perp$) of the LC director increases, a dipole moment angle along the direction of the long axis (optical axis) also increases. As illustrated in FIGS. 5A and 5B, a tilt angle of the LC director may decrease ($\theta \rightarrow \theta'$) by a locally vertical electric field that is associated with such an increase in the dipole moment angle. Accordingly, compared with the positive type IPS mode LCD that does not include the exemplary positive LC molecule including the one-sided distributed fluorine substituent, transmittance may be increased.

Table 5 shows transmittance and driving voltage in the positive type of IPS mode LCD as the vertical dielectric constant ($\epsilon\perp$) and the horizontal dielectric constant ($\epsilon\|$) increase. FIG. 6 is a graph illustrating how transmittance varies according to the average dielectric constant of the LC composition. FIG. 6 illustrates the data in Table 5 below in the form or a graph.

The average dielectric constant ($\bar{\epsilon}$) may be represented by Equation 1.

$$\bar{\epsilon} = \frac{\epsilon\| + 2\epsilon\perp}{3} \quad \text{Equation 1}$$

also includes at least one positive LC molecule having the horizontal dielectric constant ($\epsilon\|$) of about 20 or more represented by Chemical Formula C or Chemical Formula D, transmittance may be improved without increasing the driving voltage.

Referring back to FIGS. 1 and 2, the pixel electrode 191 receives the data voltage from the drain electrode 175, and the common electrode 270 receives the constant common voltage from a common voltage application unit that is placed outside the display area.

As the field generating electrodes, the pixel electrode 191 and the common electrode 270 generate an electric field so the LC molecules of the LC layer 3 disposed on the two field generating electrodes 191 and 270 may rotate in a direction that is perpendicular to or parallel to the electric field. Depending on the rotating direction of the LC molecules, polarization of light transmitted through the LC layer varies.

As such, transmittance of the LCD may increase and a wide viewing angle may be realized by forming the two field generating electrodes 191 and 270 on the single display panel 100.

According to the LCD of the illustrated exemplary embodiment, the common electrode 270 has the flat planar shape and the pixel electrode 191 has the plurality of branch electrodes, but according to another exemplary embodiment of an LCD, the pixel electrode 191 may have a flat planar shape and the common electrode 270 may have a plurality of branch electrodes.

The present invention may be applicable to all other cases in which the two field generating electrodes overlap each other on the first substrate 110 with an insulating layer interposed therebetween, the first field generating electrode formed under the insulating layer has a flat planar shape, and the second field generating electrode formed on the insulating layer has a plurality of branch electrodes.

Polarizers (not shown) may be provided at outer surfaces of the display panels 100 and 200. Transmissive axes of the polarizers are perpendicular to each other, and either one of the transmissive axes may be parallel to the gate line 121. In reflective LCDs, one of the two polarizers may be omitted.

FIG. 7 is a schematic cross-sectional view of an exemplary IPS mode LCD that is a modification of the exemplary embodiment of FIG. 3.

TABLE 5

| Average dielectric constant | Reference example (E) | E−1.5 | E−1.0 | E−0.5 | E+0.5 | E+1.0 | E+1.5 | E+2.5 | E+2.5 |
|---|---|---|---|---|---|---|---|---|---|
| $\epsilon\|$ | 7.4 | 5.9 | 6.4 | 6.9 | 7.9 | 8.4 | 8.9 | 9.4 | 9.9 |
| $\epsilon\perp$ | 2.9 | 1.4 | 1.9 | 2.4 | 3.4 | 3.9 | 4.4 | 4.9 | 5.4 |
| Average dielectric constant (E) | 4.4 | 2.9 | 3.4 | 3.9 | 4.9 | 5.4 | 5.9 | 6.4 | 6.9 |
| Transmittance (%) | 0 | −8.4 | −4.6 | −1.9 | 1.5 | 2.7 | 3.6 | 4.3 | 5.0 |
| driving voltage (V) | 4.8 | 5.1 | 5 | 4.9 | 4.8 | 4.8 | 4.8 | 4.9 | 4.9 |

Referring to Table 5 and FIG. 6, as the average dielectric constant of the LC composition ($\bar{\epsilon}$) increases, transmittance improves. In addition, as the vertical dielectric constant ($\epsilon\perp$) and the horizontal dielectric constant ($\epsilon\|$) simultaneously increase, the driving voltage may not be increased, but may be maintained at a low level. Accordingly, since the exemplary LCD not only includes the polar LC molecule containing the one-sided distributed fluorine substituent, but Referring to FIG. 7, unlike the PLS mode LCD which is described in FIG. 3, a positive type of IPS mode LCD is shown in which a pixel electrode 191 and a common electrode 270 are both formed as linear field generating electrodes. Since the current exemplary embodiment generates a horizontal electric field and the alignment direction of the alignment layer is parallel to the linear electrode, as in the exemplary embodiment of FIG. 3, the IPS LCD may be formed using the above-described exemplary LC composition.

An exemplary embodiment of an LC composition and its corresponding physical properties will now be described.

Table 6 shows the components in the LC compositions of Exemplary Embodiment 1, Exemplary Embodiment 2, and a comparative example. In Table 6, $R_1$ and $R_2$ represent an alkyl group, and the numbers in the columns labeled $R_1$ and $R_2$ represent the number of carbon atoms in the alkyl group.

TABLE 6

| Series | LC molecule | $R_1$ | $R_2$ | Comparative Example (wt %) | Exemplary embodiment 1 (wt %) | Exemplary embodiment 2 (wt %) |
|---|---|---|---|---|---|---|
| Neutral | $C_3H_7$–[cyclohexyl]–[cyclohexyl]–CH=CH$_2$ | — | — | 36.2 | 37 | 31.5 |
| | $C_3H_7$–[cyclohexyl]–[cyclohexyl]–[cyclohexyl]–CH=CH$_2$ | — | — | 9.4 | 2 | — |
| | $R_1$–[cyclohexyl]–[phenyl]–[phenyl]–$R_2$ | 3<br>5 | 2<br>2 | 4.5<br>4.5 | —<br>— | —<br>— |
| | CH$_2$=CH–[cyclohexyl]–[cyclohexyl]–[phenyl]–CH$_3$ | — | — | 5.2 | — | — |
| | $C_3H_7$–[phenyl]–[phenyl(F)]–[phenyl]–$C_3H_7$ | — | — | 3.2 | — | — |
| | $C_2H_5$–[phenyl]–[phenyl(F)]–[phenyl]–CH$_2$CH=CHCH$_3$ | — | — | — | 8 | 8 |
| | $C_3H_7$–[phenyl]–[phenyl(F)]–[phenyl]–CH$_2$CH=CHCH$_3$ | — | — | — | 8 | 8 |
| Positive polarity | $R_1$–[phenyl]–[phenyl(F)]–[phenyl(F,F,F)]–F | 2<br>3<br>5 | —<br>—<br>— | 2.4<br>7.5<br>8.0 | —<br>—<br>— | —<br>—<br>— |
| | $C_3H_7$–[cyclohexyl]–[phenyl]–[phenyl(F,F,F)]–F | — | — | 5.0 | — | — |
| | $C_3H_7$–[cyclohexyl]–[cyclohexyl]–[phenyl]–OCF$_3$ | — | — | 4.5 | 5 | 7 |

TABLE 6-continued

| Series | LC molecule | R₁ | R₂ | Comparative Example (wt %) | Exemplary embodiment 1 (wt %) | Exemplary embodiment 2 (wt %) |
|---|---|---|---|---|---|---|
| | C₃H₇–[Cy]–[Cy]–[Ph(F,F,F)]–F | — | — | 7 | 10 | 6.5 |
| | R₁–[Cy]–[Cy]–[Ph(F)]–[Ph(F,F,F)]–F | 2<br>3 | —<br>— | —<br>2.1 | 4<br>4 | 4<br>4 |
| | C₃H₇–[Ph]–[Ph(F,F)]–CF₂O–[Ph(F,F)]–F | — | — | — | 3 | 3 |
| | C₃H₇–[Ph]–[Ph(F)]–[Ph(F,F)]–CF₂O–[Ph(F,F)]–F | — | — | — | 8 | — |
| | C₃H₇–[Pyran-O]–[Ph]–[Ph(F,F)]–CF₂O–[Ph(F,F)]–F | — | — | — | — | 11 |
| Negative polarity | C₂H₅–C(F,F)–[Cy]–[Ph(F,F)]–O–C₂H₅ | — | — | — | 11 | 17 |

Table 7 shows the physical properties of the LC composition for the comparative example, Exemplary Embodiment 1, and Exemplary Embodiment 2, and a negative type IPS mode.

TABLE 7

| | Comparative Example | Negative PLS | Exemplary Embodiment 1 | Exemplary Embodiment 2 |
|---|---|---|---|---|
| $\Delta n$ | 0.110 | 0.110 | 0.110 | 0.110 |
| $\Delta \varepsilon$ | +4.5 | −3.0 | +4.5 | +4.5 |
| $\varepsilon_\parallel$ | 7.4 | 3.5 | 8.5 | 9.1 |
| $\varepsilon_\perp$ | 2.9 | 6.5 | 4.0 | 4.6 |
| Rotational viscosity Y1 (mPa·s) | 55 | 97 | 69 | 89 |
| Tni (° C.) | 79.5 | 75 | 76.8 | 74.9 |
| Driving voltage (V) | 5.0 V | 7.0 V | 5.0 V | 5.0 V |
| Transmittance | 100% | 108% | 103% | 104% |

Referring to the Table 7, LCDs including the LC compositions of Exemplary Embodiments 1 and 2 may allow a design with increased transmittance at the same driving voltage as the comparative example. Although the negative type PLS mode LCD is superior in terms of transmittance, it has a drawback in that it has a high driving voltage.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A liquid crystal composition comprising at least one polar liquid crystal molecule containing a fluorine substituent represented by Chemical Formula A or Chemical Formula B:

Formula A

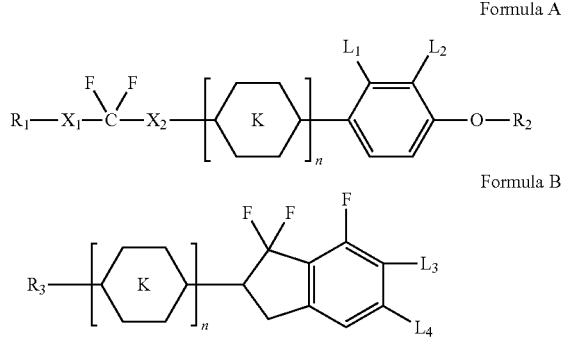

Formula B

3. The liquid crystal composition of claim 2, further comprising at least one liquid crystal molecule represented by Chemical Formula E:

Chemical Formula E

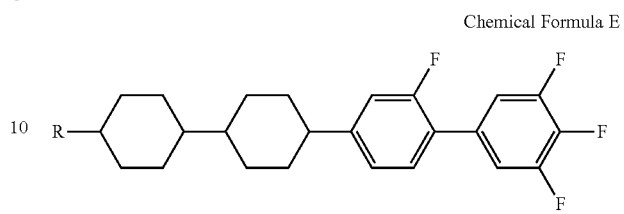

wherein, in Chemical Formula E, R is an alkyl or alkoxy group having 1 to 9 carbon atoms or an alkenyl group having 2 to 9 carbon atoms.

4. The liquid crystal composition of claim 3, further comprising at least one liquid crystal molecule represented by Chemical Formula F:

wherein, in Chemical Formulas A and B, each K is, independently of one another, 1,4-cyclohexylene or 1,4-phenylene, and groups connected to a carbon ring of the 1,4-cyclohexylene or 1,4-phenylene are all hydrogen or at least one of the groups is a fluorine, and n is 1 or 2;

in Chemical Formula A, $X_1$ is —$CF_2$—, —$CH_2O$—, or —$OCH_2$—, $X_2$ is a single bond, $L_1$ and $L_2$ are, independently of one another, —H, —F, —$CF_3$, or —$OCF_3$, and $R_1$ and $R_2$ are, independently of one another, an alkyl or alkoxy group having 1 to 9 carbon atoms or an alkenyl group having 2 to 9 carbon atoms; and in Chemical Formula B, $L_3$ and $L_4$ are —H, —F, —$CF_3$, or —$OCF_3$, wherein when $L_3$ is H or F, $L_4$ is —F, —$CF_3$, or —$OCF_3$, and $R_3$ is an alkyl group having 1 to 9 carbon atoms, an alkoxy group having 1 to 9 carbon atoms, or an alkenyl group having 2 to 9 carbon atoms.

2. The liquid crystal composition of claim 1, further comprising at least one positive liquid crystal molecule represented by Chemical Formula C or Chemical Formula D:

Chemical Formula C

Chemical Formula F

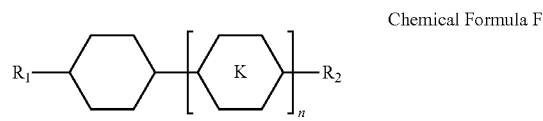

wherein, in Chemical Formula F, K is 1,4-cyclohexylene or 1,4-phenylene, $R_1$ and $R_2$ are, independently of one another, an alkyl or alkoxy group having 1 to 9 carbon atoms or an alkenyl group having 2 to 9 carbon atoms, and n is 1 or 2.

5. The liquid crystal composition of claim 4, further comprising at least one liquid crystal molecule represented by Chemical Formula G:

Chemical Formula G

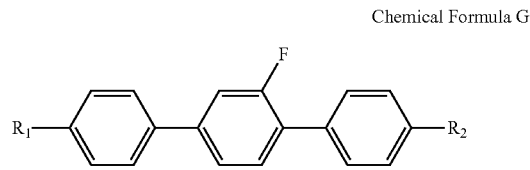

wherein, in Chemical Formula G, $R_1$ and $R_2$ are, independently of one another, an alkyl or alkoxy group having 1 to 9 carbon atoms or an alkenyl group having 2 to 9 carbon atoms.

6. The liquid crystal composition of claim 5, wherein the at least one polar liquid crystal molecule containing the fluorine substituent is present in an amount of about 5 wt % to about 30 wt % of the total weight of the liquid crystal composition.

7. A liquid crystal display comprising:
a first substrate;
a first electrode and a second electrode disposed on the first substrate;
an insulating layer interposed between the first electrode and the second electrode;
a second substrate facing the first substrate; and
a liquid crystal layer disposed between the first and second substrates, wherein the liquid crystal layer comprises at least one polar liquid crystal molecule containing a fluorine substituent represented by Chemical Formula A or Chemical Formula B:

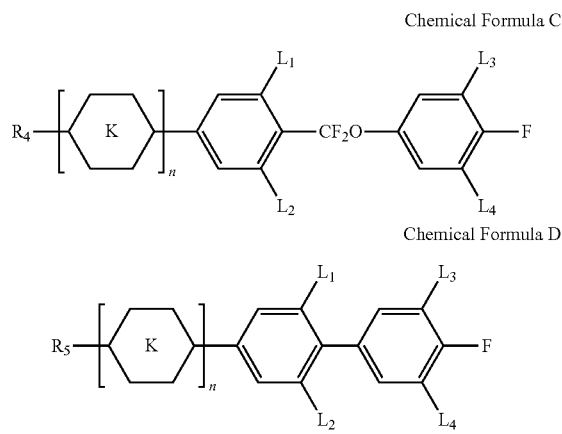

Chemical Formula D wherein, in Chemical Formula C and Chemical Formula D, each K is, independently of one another, 1,4-cyclohexylene, 1,4-phenylene, tetrahydropyran, or pyran, groups connected to a carbon ring of the 1,4-cyclohexylene, 1,4-phenylene, tetrahydropyran, or pyran are all hydrogen or at least one of the groups is fluorine, $L_1$ to $L_4$ are, independently of one another, —H, —F, —$CF_3$, or —$OCF_3$, n is 1 or 2, and $R_4$ and $R_5$ are, independently of one another, an alkyl or alkoxy group having 1 to 9 carbon atoms, or an alkenyl group having 2 to 9 carbon atoms.

Chemical Formula A

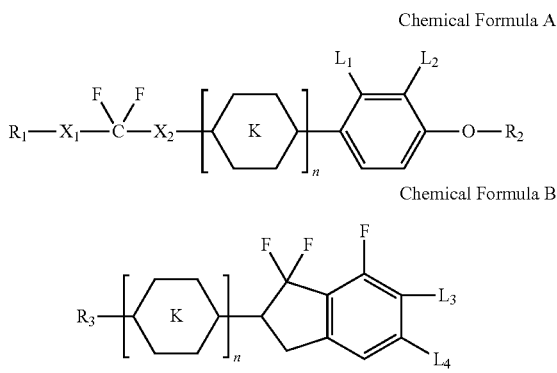

Chemical Formula B

9. The liquid crystal display of claim 8, wherein the liquid crystal layer further comprises at least one liquid crystal molecule represented by Chemical Formula E:

Chemical Formula E

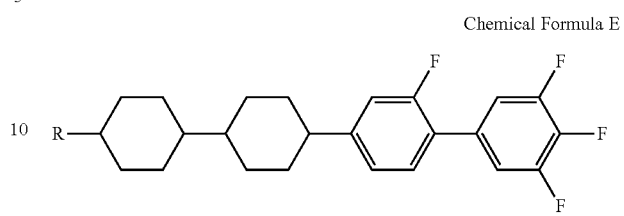

wherein, in Chemical Formula E, R is an alkyl or alkoxy group having 1 to 9 carbon atoms or an alkenyl group having 2 to 9 carbon atoms.

10. The liquid crystal display of claim 9, wherein the liquid crystal layer further comprises at least one liquid crystal molecule represented by Chemical Formula F:

wherein, in Chemical Formulas A and B, each K is, independently of one another, 1,4-cyclohexylene or 1,4-phenylene, groups connected to a carbon ring of the 1,4-cyclohexylene or 1,4-phenylene are all hydrogen or at least one of the groups is fluorine, and n is 1 or 2; in Chemical Formula A, $X_1$ is —$CF_2$—, —$CH_2O$—, or —$OCH_2$—, $X_2$ is a single bond, $L_1$ and $L_2$ are, independently of one another, —H, —F, —$CF_3$, or —$OCF_3$, and $R_1$ and $R_2$ are, independently of one another, an alkyl or alkoxy group having 1 to 9 carbon atoms or an alkenyl group having 2 to 9 carbon atoms; and in Chemical Formula B, $L_3$ and $L_4$ are —H, —F, —$CF_3$, or —$OCF_3$, wherein when $L_3$ is H or F, $L_4$ is —F, —$CF_3$, or —OCF3, and $R_3$ is an alkyl group having 1 to 9 carbon atoms, an alkoxy group having 1 to 9 carbon atoms, or an alkenyl group having 2 to 9 carbon atoms.

8. The liquid crystal display of claim 7, wherein the liquid crystal layer further comprises at least one positive liquid crystal molecule represented by Chemical Formula C or Chemical Formula D:

Chemical Formula F

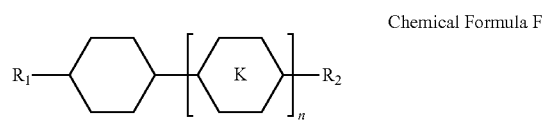

wherein, in Chemical Formula F, K is 1,4-cyclohexylene or 1,4-phenylene, and $R_1$ and $R_2$ are, independently of one another, an alkyl or alkoxy group having 1 to 9 carbon atoms or an alkenyl group having 2 to 9 carbon atoms, and n is 1 or 2.

11. The liquid crystal display of claim 10, wherein the liquid crystal layer further comprises at least one liquid crystal molecule represented by Chemical Formula G:

Chemical Formula C

Chemical Formula G

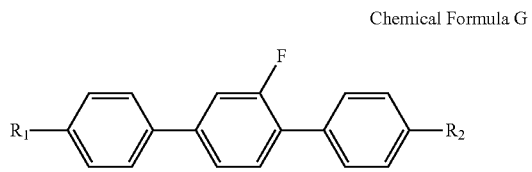

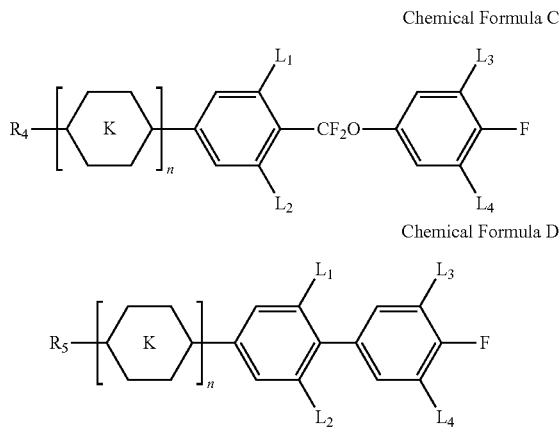

Chemical Formula D wherein, in Chemical Formula G, $R_1$ and $R_2$ are, independently of one another, an alkyl or alkoxy group having 1 to 9 carbon atoms or an alkenyl group having 2 to 9 carbon atoms.

12. The liquid crystal display of claim 11, wherein the polar liquid crystal molecule containing the fluorine substituent is present in an amount of about 5 wt % to about 30 wt % of the total weight of the liquid crystal layer.

13. The liquid crystal display of claim 7, wherein the insulating layer is disposed on the first electrode and the second electrode is disposed on the insulating layer.

14. The liquid crystal display of claim 13, wherein the first electrode is plate-shaped and the second electrode includes a plurality of branch electrodes.

wherein, in Chemical Formula C and Chemical Formula D, each K is independently, 1,4-cyclohexylene, 1,4-phenylene, tetrahydropyran, or pyran, groups connected to a carbon ring included in 1,4-cyclohexylene, 1,4-phenylene, tetrahydropyran, or pyran are all hydrogen or at least one of the groups is fluorine, $L_1$ to $L_4$ are, independently of one another, —H, —F, —$CF_3$, or —$OCF_3$, n is 1 or 2, and $R_4$ and $R_5$ are, independently of one another, an alkyl or alkoxy group having 1 to 9 carbon atoms or an alkenyl group having 2 to 9 carbon atoms.

15. The liquid crystal display of claim 14, wherein the plurality of branch electrodes overlap the plate-shaped first electrode.

16. The liquid crystal display of claim 15, wherein the second electrode is electrically connected to a thin film transistor by a contact hole defined in the insulating layer.

17. The liquid crystal display of claim 16, wherein liquid crystal molecules included in the liquid crystal layer are tilted in a direction parallel to the branch electrodes when no electric field is applied to the liquid crystal layer.

18. The liquid crystal display of claim 17, further comprising an alignment layer disposed on the second electrode, wherein the alignment layer is rubbed or photo-aligned in a direction parallel to the branch electrodes.

19. The liquid crystal display of claim 17, wherein, when an electric field is applied to the LC layer, the LC molecules are tilted in a direction parallel to the electric field.

20. The liquid crystal display of claim 14, wherein the at least one polar liquid crystal molecule containing a fluorine substituent is represented by Chemical Formula B, Chemical Formula B

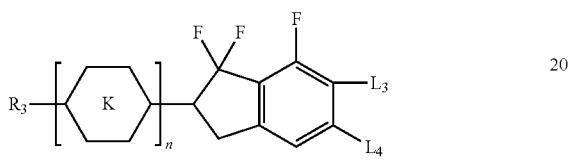

wherein, in Chemical Formula B, $L_3$ is —$CF_3$, or —$OCF_3$, $L_4$ is —H, —F, —$CF_3$, or —$OCF_3$, and $R_3$ is an alkyl group having 1 to 9 carbon atoms, an alkoxy group having 1 to 9 carbon atoms, or an alkenyl group having 2 to 9 carbon atoms, and n is 1 or 2.

* * * * *